United States Patent
Grison et al.

(10) Patent No.: US 7,049,454 B2
(45) Date of Patent: May 23, 2006

(54) ALKOXYSILACYCLOALKANES, PROCESS FOR THEIR PREPARATION AND THEIR USE FOR THE POLYMERIZATION OF OLEFINS

(75) Inventors: Claude Grison, Vandoeuvre les Nancy (FR); Valerie Barthel, Guewenheim (FR); Delphine Batt-Coutrot, Villers les Nancy (FR); Philippe Coutrot, Saulxures les Nancy (FR); Thierry Saudemont, Jurancon (FR); Jean-Michel Brusson, Idron (FR); Jean Malinge, Loubieng (FR); Claude Brun, Idron (FR); Corinne Meynard, Dax (FR)

(73) Assignee: Arkema, Puteaux (FR)

( * ) Notice: Subject to any disclaimer, the term of this patent is extended or adjusted under 35 U.S.C. 154(b) by 159 days.

(21) Appl. No.: 10/618,834

(22) Filed: Jul. 15, 2003

(65) Prior Publication Data

US 2004/0014913 A1 Jan. 22, 2004

Related U.S. Application Data

(60) Division of application No. 09/768,162, filed on Jan. 24, 2001, now Pat. No. 6,624,264, and a continuation-in-part of application No. 09/572,372, filed on May 18, 2000, now abandoned, which is a continuation-in-part of application No. 08/715,915, filed on Sep. 19, 1996, now Pat. No. 6,228,961.

(30) Foreign Application Priority Data

Sep. 20, 1995 (FR) .................................. 95 11025
May 18, 1999 (FR) .................................. 99 06279

(51) Int. Cl.
*C07F 7/18* (2006.01)
(52) U.S. Cl. .................................................... 556/406
(58) Field of Classification Search ................. 556/406
See application file for complete search history.

(56) References Cited

U.S. PATENT DOCUMENTS

| | | | |
|---|---|---|---|
| 2,464,231 A * | 3/1949 | Herah ........................ 556/406 |
| 3,687,995 A | 8/1972 | Jonas et al. |
| 3,694,427 A | 9/1972 | Jonas et al. |
| 4,011,360 A | 3/1977 | Walsh |
| 4,490,475 A | 12/1984 | Bailly et al. |
| 4,497,904 A | 2/1985 | Blaya et al. |
| 4,511,703 A | 4/1985 | Bailly |
| 4,526,954 A | 7/1985 | Williams |
| 4,673,662 A | 6/1987 | Bailly |
| 4,721,763 A | 1/1988 | Bailly et al. |
| 4,777,278 A | 10/1988 | Band et al. |
| 4,829,038 A * | 5/1989 | Hoppin et al. ............... 502/125 |
| 4,958,041 A | 9/1990 | Graefe et al. |
| 5,059,705 A | 10/1991 | Okinoshima et al. |
| 5,087,522 A | 2/1992 | Bailly et al. |
| 5,208,109 A | 5/1993 | Bailly et al. |
| 5,212,132 A | 5/1993 | Spitz et al. |
| 5,212,133 A | 5/1993 | Duranel et al. |
| 5,296,624 A | 3/1994 | Larson et al. |
| 5,346,972 A | 9/1994 | Duranel et al. |
| 5,498,770 A | 3/1996 | Hosaka et al. |
| 5,773,537 A | 6/1998 | Mueller et al. |
| 5,868,961 A | 2/1999 | Shimizu et al. |
| 6,228,961 B1 | 5/2001 | Grison et al. |

FOREIGN PATENT DOCUMENTS

| | | |
|---|---|---|
| EP | 0 250 229 A1 | 12/1987 |
| EP | 250 229 * | 12/1987 |
| EP | 0 348 693 B1 | 1/1990 |
| EP | 0 361 493 A1 | 4/1990 |
| EP | 0 665 243 A2 | 8/1995 |
| EP | 0 765 881 A1 | 4/1997 |
| FR | 2.069.504 | 9/1971 |
| JP | 11-199590 | 7/1999 |

OTHER PUBLICATIONS

*Handbook of Chemistry and Physics*, 61$^{st}$ Ed., 1980-1981, Periodic Table of Elements.
B.H. Lipshutz, "Synthetic procedures involving oganocopper reagents", *Organometallis in Synthesis*, Wiley & Sons, 1994, p. 283.
K. Abe, Synthesis, 1998, p. 231.
*Chemical Abstracts*, vol. 50/No. 12, 1956, Abstract 8270e.
*Chemical Abstracts*, vol. 46, 1952, Abstract 6082i.
R. West, "Cyclic Organosilicon Compounds," *J. Am. Soc.*, vol. 76, 1954, pp. 6012-6014.
B. Nguyen et alii, "A Convenient Synthetic Route To Methylated Silacyclohexanes," *J. Org. Chem.*, vol. 51, 1986, pp. 2206-2210.
*Encyclopedia of Polymer Science and Engineering*, vol. 15, Wiley & Sons Pub., 1989, pp. 226-228.
Encyclopedia of Chemical Technology, vol. 20, Wiley & Sons Pub., 1982, pp. 922, 927 and 928.
English-language Translation of French Application No. 2,069,504 (Sep. 1971), French Application.
English-language Translation of European Patent No. 0 348 693 (Jan. 1990), European Patent.

* cited by examiner

*Primary Examiner*—Margaret G. Moore
(74) *Attorney, Agent, or Firm*—Smith, Gambrell & Russell, LLP

(57) ABSTRACT

The invention relates to alkoxysilacycloalkanes, to the process of their preparation and to their use in the polymerization of olefins. The introduction of these alkoxysilacycloalkanes into the olefin polymerization environment makes it possible to raise the heptane-insolubles content of the polymer finally formed.

2 Claims, No Drawings

ALKOXYSILACYCLOALKANES, PROCESS FOR THEIR PREPARATION AND THEIR USE FOR THE POLYMERIZATION OF OLEFINS

CROSS REFERENCE TO RELATED APPLICATION

This application is a division of U.S. application Ser. No. 09/768,162, filed Jan. 24, 2001 now U.S. Pat. No. 6,624,264, which is a continuation-in-part of U.S. application Ser. No. 08/715,915, filed Sep. 19, 1996 now U.S. Pat. No. 6,228,961, and also a continuation-in-part of U.S. application Ser. No. 09/572,372, filed May 18, 2000 now abandoned, which are being incorporated in their entirety herein by reference.

FIELD OF THE INVENTION

The invention relates to alkoxysilacycloalkanes, to the process for their preparation and to their use as electron-donor in processes for the polymerization or copolymerization of olefins like propylene or ethylene.

BACKGROUND OF THE INVENTION

A polyolefin which has an excessively high content of heptane-solubles may have a tendency to stick and is therefore difficult to convey and, as a result, is not very suitable for industrial applications. In addition, in the alimentary field, the presence of solubles in a polyolefin which is intended to come into contact with foodstuffs is deemed to be undesirable. For these reasons, for example, isotactic polypropylene preferably has a heptane-insolubles content (denoted by HI, from the expression "heptane-insoluble") higher than 80% by weight.

Patent Application EP 250229 teaches that the use of certain silanes during the polymerization of olefins allows the hexane-solubles content of the polyolefin obtained to be reduced.

The paper by R. West, Journal of the American Chemical Society (1954) 76, 6012, describes a method for the preparation of 1,1-dimethoxysilacyclohexane. This preparation involves numerous stages and the intermediate formation of a chlorosilacycloalkane which is particularly tricky to handle and easily degradable.

The process of the present invention is particularly simple, involves raw materials which are easily available and relatively stable and does not involve any chlorosilacycloalkane. The stability of the materials used reduces the risk of side reactions, thereby tending in the direction of better purity of the products which are finally prepared.

The presence of alkoxysilacycloalkanes in the environment for the polymerization or copolymerization of at least one olefin is reflected in an appreciable increase in the polyolefin yield and in an appreciable increase in the HI of the said polyolefin in addition, the alkoxysilacycloalkane acts as a morphology protector in the suspension and gas-phase polymerization or copolymerization processes. This means that, in the case of these so-called heterogeneous processes, the polymer or copolymer formed is a better morphological replica of the initial solid catalytic component if an alkoxysilacycloalkane is introduced as an external electron-donor into the polymerization or copolymerization environment.

The process according to the invention includes the stage of reaction between an alkylenedimagnesium dibromide of formula Br—Mg-A-Mg—Br in which A is a divalent alkylene radical optionally substituted, for example by an alkyl radical containing, for example, from 1 to 6 carbon atoms, the said alkylene radical containing from 4 to 7 carbon atoms, the optional substituent(s) being excluded, and a tetraalkoxysilane of formula $(OR^1)(OR^2)(OR^3)(OR^4)Si$ in which $R^1$, $R^2$, $R^3$ and $R^4$, which may be identical or different, denote linear or branched, saturated and/or unsaturated hydrocarbon radicals which may include a ring.

The radicals $R^1$, $R^2$, $R^3$ and $R^4$ preferably are alkyl radicals containing from 1 to 6 carbon atoms.

The reaction may be carried out in a solvent which preferably exhibits a Lewis base character, as is the case with ethers. The solvent may, for example, be diethyl ether.

The quantity of inert solvent which is employed may, for example, be such that, assuming the reaction yield to be equal to 100%, the alkoxysilacycloalkane formed is encountered again in a concentration of between 0.05 and 2 moles/liter.

The reaction may be carried out, for example, between 0 and 50° C. for 10 min to 12 hours, if appropriate under pressure if the volatility of the species used makes this necessary, bearing in mind the temperature chosen. Since the reaction is generally exothermic, it is preferable to bring the dibromide and the tetraalkoxysilane into contact gradually and with stirring so as to retain control of the temperature of the mixture. The reaction results in the formation of at least one alkoxysilacycloalkane of formula

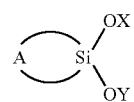

(I)

in which X and Y denote groups forming part of the group of the radicals $R^1$, $R^2$, $R^3$ and $R^4$ and in which A retains the meaning given above. The ring of the alkoxysilacycloalkane therefore contains a silicon atom and a number of carbon atoms equal to the number of carbon atoms which the alkylene radical A contained, the optional substituents of the said alkylene radical being excluded.

The alkoxysilacycloalkanes in the case of which A is an alkylene radical containing at least one alkyl substituent are also a subject-matter of the present invention.

By way of example, Table 1 below mentions some alkoxysilacycloalkanes which can be prepared by the process according to the invention, by reaction of tetramethoxysilane with an alkylenedimagnesium dibromide, depending on the nature of the divalent alkylene radical A included in the alkylenedimagnesium dibromide.

TABLE 1

| Nature of A | Alkoxysilacycloalkane formed |
|---|---|
| tetramethylene | 1,1-dimethoxysilacyclopentane |
| 1-methyltetramethylene | 1,1-dimethoxy-2-methylsilacyclopentane |
| 1-ethyltetramethylene | 1,1-dimethoxy-2-ethylsilacyclopentane |
| 1-n-propyltetramethylene | 1,1-dimethoxy-2-n-propylsilacyclopentane |
| 1-isopropyltetramethylene | 1,1-dimethoxy-2-isopropylsilacyclopentane |
| 1-n-butyltetramethylene | 1,1-dimethoxy-2-n-butylsilacyclopentane |
| pentamethylene | 1,1-dimethoxysilacyclohexane |
| 1-methylpentamethylene | 1,1-dimethoxy-2-methylsilacyclohexane |
| 1-ethylpentamethylene | 1,1-dimethoxy-2-ethylsilacyclohexane |

TABLE 1-continued

| Nature of A | Alkoxysilacycloalkane formed |
|---|---|
| 1-n-propylpentamethylene | 1,1-dimethoxy-2-n-propylsilacyclohexane |
| 1-isopropylpentamethylene | 1,1-dimethoxy-2-isopropylsilacyclohexane |
| 1-n-butylpentamethylene | 1,1-dimethoxy-2-n-butylsilacyclohexane |
| 2,3-dimethyltetramethylene | 1,1-dimethoxy-3,4-dimethylsilacyclopentane |
| 1,4-dimethyltetramethylene | 1,1-dimethoxy-2,5-dimethylsilacyclopentane |
| hexamethylene | 1,1-dimethoxysilacycloheptane |

The reaction also gives rise to the formation of BrMgOZ in which Z is a radical forming part of the group of the radicals $R^1$, $R^2$, $R^3$ and $R^4$. This BrMgOZ, considered as being a by-product in the context of the present invention, is generally solid and can, in this case, be removed, for example by filtration. After evaporation of the optional solvent employed and of any excess reactants, the alkoxysilacycloalkane may be purified by distillation, preferably at reduced pressure, for example between 1 and $1 \times 10^3$ mbar.

The alkylenedimagnesium dibromide of formula Br—Mg-A-Mg—Br may be prepared, for example, by reaction between a dibromoalkane of formula Br-A-Br and magnesium in the presence of a solvent, for example an ether like diethyl ether, for example between 0 and 50° C., if appropriate under pressure if the volatility of the species used demands this, bearing in mind the temperature chosen.

The alkoxysilacycloalkanes capable of being obtained by the process according to the invention may be used as an electron-donor in the polymerization or copolymerization of at least one olefin. For example, the silacycloalkane may be introduced within a solid catalytic component of the Ziegler-Natta type and may act as an internal electron-donor.

It is also possible to employ it as an external electron-donor in an environment for the polymerization or copolymerization of at least one olefin, so as to reduce the hexane-solubles content of the polymer or copolymer finally prepared.

In the case of this latter application (external electron-donor) it is preferred to employ an alkoxysilacycloalkane of formula (I) in which X and Y denote methyl radicals.

The alkoxysilacycloalkane preferably contains at least one alkyl substituent positioned alpha to the silicon atom. Particularly high HI values are obtained when the alkyl substituent contains at least two carbon atoms. An excellent compromise of properties (very high HI and generally high yield) is obtained when the alkyl substituent contains 2 or 3 carbon atoms, as is the case with 1,1-dimethoxy-2-ethylsilacyclopentane, 1,1-dimethoxy-2-n-propylsilacyclopentane, 1,1-dimethoxy-2-isopropylsilacyclopentane, 1,1-dimethoxy-2-ethylsilacyclohexane, 1,1-dimethoxy-2-n-propylsilacyclohexane and 1,1-dimethoxy-2-isopropylsilacyclohexane.

In accordance with a specific aspect of the present invention there is provided a process for polymerizing at least one olefin in the presence of a catalyst and of a dialkoxysilacyclohexane of the formula

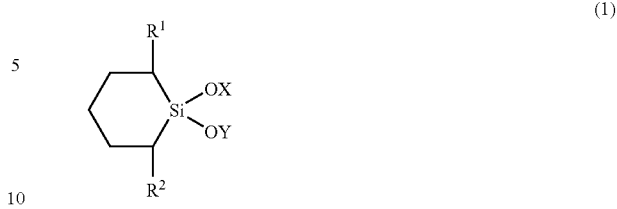

in which $R^1$ and $R^2$, which may be identical or different, represent alkyl radicals containing 1 to 5 carbon atoms, and X and Y, which may be identical or different, are alkyl radicals containing 1 to 6 carbon atoms. $R^1$, $R^2$, X and Y may be selected from the radicals methyl, ethyl, n-propyl, isopropyl, n-butyl, tert-butyl and isobutyl. Preferably, at least one radical among $R^1$ and $R^2$ is an ethyl radical. More preferably still, $R^1$ and $R^2$ are both ethyl radicals.

The Applicant has found that the presence of the dialkoxysilacyclohexane of formula (1) in the polymerization medium resulted in a polymer having a higher heptane insolubility index coupled with, in general, a greater productivity, in comparison with an identical process in which the dialkoxysilacyclohexane was replaced by the same number of moles of a dialkoxysilacyclohexane of identical structure but in which at least one of the radicals $R^1$ and $R^2$ was replaced by a hydrogen atom.

The following dialkoxysilacyclohexanes may be used:
1,1-dimethoxy-2,6-dimethylsilacyclohexane,
1,1-dimethoxy-2,6-diethylsilacyclohexane,
1,1-dimethoxy-2,6-di-n-propylsilacyclohexane,
1,1-dimethoxy-2,6-diisopropylsilacyclohexane,
1,1-dimethoxy-2,6-di-n-butylsilacyclohexane,
1,1-dimethoxy-2-ethyl-6-methylsilacyclohexane,
1,1-dimethoxy-2-ethyl-6-n-propylsilacyclohexane,
1,1-dimethoxy-2-ethyl-6-isopropylsilacyclohexane,
1,1-dimethoxy-2-n-butyl-6-ethylsilacyclohexane,
1,1-diethoxy-2,6-dimethylsilacyclohexane,
1,1-diethoxy-2,6-diethylsilacyclohexane,
1,1-diethoxy-2,6-di-n-propylsilacyclohexane,
1,1-diethoxy-2,6-diisopropylsilacyclohexane,
1,1-diethoxy-2,6-di-n-butylsilacyclohexane,
1,1-diethoxy-2-ethyl-6-methylsilacyclohexane,
1,1-diethoxy-2-ethyl-6-n-propylsilacyclohexane,
1,1-diethoxy-2-ethyl-6-isopropylsilacyclohexane, and
1,1-diethoxy-2-n-butyl-6-ethylsilacyclohexane.

1,1-Dimethoxy-2,6-diethylsilacyclohexane is particularly preferred.

The dialkoxysilacyclohexane acts as an electron donor during the polymerization. When the catalyst comprises a solid catalytic component, of the Ziegler-Natta type, for example, the dialkoxysilacyclohexane may be incorporated inside the said solid component and be able to act as an internal electron donor.

It is also possible to have the dialkoxysilacyclohexane act as an external electron donor in order to reduce the proportion of heptane solubles in the polymer finally prepared. In this latter case, the dialkoxysilacyclohexane may be introduced into the polymerization medium independently of the solid catalytic component. When the catalyst system involves a solid catalytic component and a cocatalyst, it is also possible to effect precontact between the solid catalytic component, the catalyst and the dialkoxysilacyclohexane before entry into the polymerization medium.

The alkoxysilacycloalkane is generally introduced in a proportion of $1 \times 10^{-4}$ to 0.2 millimoles per mole of olefin to be polymerized or copolymerized. If the alkoxysilacycloalkane has been prepared in the presence of a solvent of basic character in the Lewis sense, it is recommended to remove the latter before the polymerization or copolymerization stage because it may have an undesirable influence on the structure of the polymers formed. On the other hand, the alkoxysilacycloalkane may be introduced in the presence, for example, of an aliphatic, alicyclic or aromatic hydrocarbon solvent which is not obviously of a basic nature in the Lewis sense, like hexane, cyclohexane or toluene.

A solid catalytic component containing a transition metal is generally introduced into the polymerization or copolymerization environment.

The transition metal may be chosen from the elements of groups 3b, 4b, 5b, 6b, 7b and 8, lanthanides and actinides, of the Periodic Classification of the elements, as defined in the Handbook of Chemistry and Physics, sixty-first edition, 1980–1981. These transition metals are preferably chosen from titanium, vanadium, hafnium, zirconium and chromium.

The solid catalytic component may be of the Ziegler-Natta type and may, for example, be in the form of a complex containing at least the elements Mg, Ti and Cl, the titanium being in the $Ti^{IV}$ and/or $Ti^{III}$ chlorinated form. The solid component may include an electron-donor or acceptor.

A catalytic component of the Ziegler-Natta type is usually the result of the combination of at least one titanium compound, a compound of magnesium and chlorine and optionally an aluminium compound and/or an electron-donor or acceptor, as well as any other compound that can be employed in a component of this type.

The titanium compound is usually chosen from the titanium chlorine compounds of formula $Ti-(OR')_xCl_{4-x}$ in which R' denotes an aliphatic or aromatic hydrocarbon radical containing from one to fourteen carbon atoms or denotes $COR^5$ with $R^5$ denoting an aliphatic or aromatic hydrocarbon radical containing from one to fourteen carbon atoms, and x denotes an integer ranging from 0 to 3.

The magnesium compound is usually chosen from the compounds of formula $Mg(OR^6)_nCl_{2-n}$, in which $R^6$ denotes hydrogen or a linear or cyclic hydrocarbon radical and n denotes an integer ranging from 0 to 2.

The chlorine present in the component of Ziegler-Natta type may originate directly from the titanium halide and/or the magnesium halide. It may also originate from an independent chlorinating agent such as hydrochloric acid or an organic halide like butyl chloride.

Depending on the nature of the transition metal included in the solid-catalytic component, it may be necessary to add to the polymerization environment a cocatalyst capable of activating the transition metal of the solid component. The catalyst of the polymerization process according to the invention may therefore be a multi-component catalyst system, such as the combination of a solid catalytic component and a cocatalyst. If the transition metal is titanium, the cocatalyst may be chosen from organic aluminium derivatives.

This organic aluminium derivative may be a derivative of formula $R^7R^8R^9Al$ in which each of $R^7$, $R^8$ and $R^9$, which may be identical or different, denotes either a hydrogen atom or a halogen atom or an alkyl group containing from 1 to 20 carbon atoms, at least one of $R^7$, $R^8$ and $R^9$ denoting an alkyl group. As an example of suitable compound there may be mentioned ethylaluminium dichloride or dibromide or dihydride, isobutylaluminium dichloride or dibromide or dihydride, diethylaluminium chloride or bromide or hydride, di-n-propylaluminium chloride or bromide or hydride, and diisobutylaluminium chloride or bromide or hydride. A trialkylaluminium such as tri-n-hexylaluminium, triisobutylaluminium, trimethylaluminium and triethylaluminium is employed in preference to the abovementioned compounds.

The cocatalyst may also be an aluminoxane. This aluminoxane may be linear, of formula

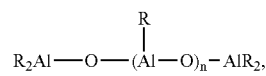

or cyclic, of formula

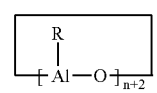

R denoting an alkyl radical containing from one to six carbon atoms and n being an integer ranging from 2 to 40, preferably from 10 to 20. The aluminoxane may include groups R of different nature. All the groups R preferably denote methyl groups. Furthermore, a cocatalyst is also intended to mean mixtures of the abovementioned compounds.

The quantities of cocatalyst which are employed must be sufficient to activate the transition metal. In general, when an organic aluminium derivative is employed as cocatalyst, a quantity thereof is introduced such that the atomic ratio of the aluminium contributed by the cocatalyst to the transition metal(s) which it is desired to activate ranges from 0.5 to 10 000 and preferably from 1 to 1000.

The polymerization or copolymerization process may be conducted in suspension, in solution, in gaseous phase or in bulk.

A bulk polymerization process consists in performing a polymerization in at least one of the olefins to be polymerized which is kept in the liquid or supercritical state.

The solution or suspension polymerization processes consist in performing a polymerization in solution or in suspension in an inert medium and especially in an aliphatic hydrocarbon.

In the case of a solution polymerization process it is possible to employ, for example, a hydrocarbon containing from eight to twelve carbon atoms or a mixture of these hydrocarbons. In the case of a suspension polymerization process it is possible to employ, for example, n-heptane, n-hexane, isohexane, isopentane or isobutane.

The operating conditions for these bulk, solution, suspension or gas-phase polymerization processes are those that are usually proposed for similar cases making use of conventional catalyst systems of the Ziegler-Natta type, whether supported or unsupported.

For example, in the case of a suspension or solution polymerization process it is possible to operate at temperatures ranging up to 250° C. and at pressures ranging from atmospheric pressure to 250 bars. In the case of a polymerization process in liquid propylene medium the temperatures may range up to the critical temperature and the pressures may be included between the atmospheric pressure and the critical pressure. In the case of a bulk polymerization process resulting in polyethylenes or in copolymers in which ethylene predominates it is possible to operate at temperatures of between 130° C. and 350° C. and at pressures ranging from 200 to 3500 bars.

A gas-phase polymerization process may be employed using any reactor which permits gas-phase polymerization, and in particular in an agitated-bed (e.g. stirred) and/or a fluidized-bed reactor.

The conditions for implementing the gas-phase polymerization, especially temperature, pressure, injection of the olefin or of the olefins into the reactor containing a stirred bed and/or a fluidized bed, and control of the polymerization temperature and pressure, are similar to those proposed in the prior art for the gas-phase polymerization of olefins. The operation is generally carried out at a temperature that is lower than the melting point Tm of the polymer prepolymer to be synthesized, and more particularly between +20° C. and (Tm−5)° C., and at a pressure such that the olefin or the olefins are essentially in the vapour phase.

The solution, suspension, bulk or gas-phase polymerization processes may involve a chain transfer agent, so as to control the melt index of the polymer to be produced. The chain transfer agent employed may be hydrogen, which is introduced in a quantity that can range up to 90% and preferably lies between 0.01 and 60 mol % of the combined olefin and hydrogen delivered to the reactor.

The olefins that can be employed for the polymerization or copolymerization are, for example, the olefins containing from two to twenty carbon atoms and in particular the alpha-olefins of this group. Olefins which may be mentioned are ethylene, propylene, 1-butene, 4-methyl-1-pentene, 1-octene, 1-hexene, 3-methyl-1-pentene, 3-methyl-1-butene, 1-decene, 1-tetradecene or mixtures thereof.

The polymerization or copolymerization process according to the invention is particularly suitable for reducing the heptane-solubles content of polymers or copolymers when the polymerization or copolymerization environment includes an olefin containing at least three carbon atoms. This process is therefore particularly suited for the polymerization or copolymerization of propylene.

In the examples which follow the heptane-insolubles content (represented by HI) was measured by extraction of the soluble fraction from the polymer using boiling heptane for two hours in an apparatus of the Kumagawa type.

EXAMPLES 1 TO 15 a) Preparation of alkylenedimagnesium dibromides

In a 500-ml glass round bottom flask fitted with a water condenser, a thermometer and a mechanical stirring system and which has been purged with argon 0.2 moles of dibromoalkane of formula Br-A-Br in the form of a solution in 200 ml of anhydrous diethyl ether are added to 0.46 moles of magnesium, and this preparation is left stirred for 6 hours at ambient temperature. The preparation is then transferred to a dropping funnel.

b) Preparation of dimethoxysilacycloalkanes

In a 1.5-liter glass round bottom flask fitted with a mechanical stirring system, a water condenser and a dropping funnel containing the preparation produced in a), and after purging with argon, the preparation produced in a) is added over 2 hours to 0.18 moles of tetramethoxysilane in the form of a solution in 400 ml of diethyl ether at ambient temperature. A heat release takes place and a precipitate appears. When the addition is finished the mixture is stirred for 30 minutes and then heated to reflux for 4 hours. The mixture is then cooled to ambient temperature, the solid being removed by filtration and washed with ether, still under argon atmosphere. The ether is removed in the rotary evaporator at approximately 25° C. at a pressure of 30 mbar. The residue contains a dimethoxysilacycloalkane of formula

(II)

Table 2 gives the boiling points (b.p.) at a pressure P, of the compounds produced, as a function of the nature of the divalent radicals A employed.

c) Polymerizations in Liquid Propylene

The following are introduced, in the order shown, into an 8-liter stainless steel reactor fitted with a stirring system and a temperature control, after the reactor has been purged with nitrogen: 2.5 l (STP) of hydrogen, 6 liters of liquid propylene, 30 millimoles of triethylaluminium in the form of a solution in hexane at a concentration of 1.5 moles/liter, and then a dimethoxysilacycloalkane as prepared in b), in the form of a solution in hexane at a concentration of 0.2 moles per liter, so as to conform to an Al/Si molar ratio shown in Table 2. After stirring for 10 minutes at ambient temperature 40 mg of a solid catalytic component prepared as in Example 12 of U.S. Pat. No. 5,212,132 are introduced. With the stirring continued, the temperature of the reactor is next raised to 70° C. over 10 minutes, kept at this temperature for an hour and then the reactor is cooled and decompressed. The results are collected in Table 2.

EXAMPLE 16

Comparative

Propylene is polymerized in conditions which are equivalent to those described in c) of the preceding examples, except that no alkoxysilacycloalkane is introduced into the polymerization environment. The results are collected in Table 2.

TABLE 2

| Example No. | PREPARATION OF ALKOXYSILACYCLOALKANES | | B.p. (° C.) | P (mbar) | POLYMERIZATIONS | | HI (weight %) |
| | Nature of A | Nature of the dimethoxysilacycloalkane obtained | | | Al/Si | Yield (g/g) | |
| --- | --- | --- | --- | --- | --- | --- | --- |
| 1 | tetramethylene | 1,1-dimethoxysilacyclopentane | 63 | 40 | 10 | 8 100 | 61.7 |
| 2 | 1-methyltetramethylene | 1,1-dimethoxy-2-methylsilacyclopentane | 80 | 33 | 10 | 20 640 | 91.3 |
| 3 | 1-ethyltetramethylene | 1,1-dimethoxy-2-ethylsilacyclopentane | 92 | 40 | 10 | 30 240 | 96.2 |
| 4 | 1-n-propyltetramethylene | 1,1-dimethoxy-2-n-propylsilacyclopentane | 104 | 40 | 10 | 24 300 | 95.1 |

TABLE 2-continued

| | | PREPARATION OF ALKOXYSILACYCLOALKANES | | | POLYMERIZATIONS | | |
|---|---|---|---|---|---|---|---|
| Example No. | Nature of A | Nature of the dimethoxysilacycloalkane obtained | B.p. (° C.) | P (mbar) | Al/Si | Yield (g/g) | HI (weight %) |
| 5 | 1-isopropyltetramethylene | 1,1-dimethoxy-2-isopropylsilacyclopentane | 95–100 | 1.3 | 23 | 36 800 | 94.1 |
| 6 | 1-n-butyltetramethylene | 1,1-dimethoxy-2-n-butylsilacyclopentane | 49–51 | 5.3 | 10 | 27 600 | 94.5 |
| 7 | pentamethylene | 1,1-dimethoxysilacyclohexane | 171 | 1013 | 10 | 10 400 | 82.3 |
| 8 | 1-methylpentamethylene | 1,1-dimethoxy-2-methylsilacyclohexane | 75–78 | 40 | 20 | 35 100 | 96.4 |
| 9 | 1-ethylpentamethylene | 1,1-dimethoxy-2-ethylsilacyclohexane | 102–105 | 40 | 20 | 42 780 | 97.9 |
| 10 | 1-n-propylpentamethylene | 1,1-dimethoxy-2-n-propylsilacyclohexane | 88–90 | 10.7 | 20 | 34 200 | 96.8 |
| 11 | 1-isopropylpentamethylene | 1,1-dimethoxy-2-isopropylsilacyclohexane | 110–115 | 40 | 20 | 29 800 | 96.5 |
| 12 | 1-n-butylpentamethylene | 1,1-dimethoxy-2-n-butylsilacyclohexane | 60–62 | 4 | | | |
| 13 | 2,3-dimethyltetramethylene | 1,1-dimethoxy-3,4-dimethylsilacyclopentane | 68–71 | 40 | 10 | 17 600 | 89.3 |
| 14 | 1,4-dimethyltetramethylene | 1,1-dimethoxy-2,5-dimethylsilacyclopentane | 70 | 40 | 10 | 27 700 | 96 |
| 15 | hexamethylene | 1,1-dimethoxysilacycloheptane | 80 | 40 | | | |
| 16 (comp.) | — | — | | | | 7 400 | 60 |

The dialkoxysilacyclohexane used in specific aspects of the present invention may be prepared by a process comprising a step A of reaction between an alkylenedimagnesium dibromide of formula

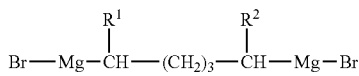

where $R^1$ and $R^2$ are as defined above, with a tetraalkoxysilane of formula $(OR^a)(OR^b)(OR^c)(OR^d)Si$, in which $R^a$, $R^b$, $R^c$ and $R^d$ are selected from the same group as X and Y, at least one of the radicals $R^a$, $R^b$, $R^c$ and $R^d$ being identical to X, and at least one of the radicals $R^a$, $R^b$, $R^c$ and $R^d$ being identical to Y. Preferably, X and Y are identical, and in that case, preferably, $R^a$, $R^b$, $R^c$ and $R^d$ are also both identical to X and Y.

For the reaction of this stage A, it is possible, for example, to deploy the reactants such that the molar ratio of the alkylenedimagnesium dibromide to the tetraalkoxysilane is preferably from 1 to 3.

This reaction is preferably carried out in the presence of a solvent, which may be an ether such as diethyl ether or tetrahydrofuran (THF), it being possible for the said solvent to be introduced in an amount such that the total magnesium concentration during the entire reaction is preferably between 0.05 and 1.2 mol per liter. Before the reaction, the reactants may be dissolved, separately, in the solvent and introduced in this form, in solution, into the reaction medium. For example, before carrying out reaction, the alkylenedimagnesium dibromide may be in solution in the solvent in an amount of from 0.1 to 1.2 mol per liter, and the tetraalkoxysilane may be in solution in the solvent in an amount of 0.1 mol per liter. This reaction may be conducted, for example, at between 30 and 70° C., although the boiling point of the solvent may constitute an upper temperature limit if the reaction is conducted at atmospheric pressure.

By way of example, Table 1 below indicates a number of dialkoxysilacyclohexanes which can be prepared by reacting tetramethoxysilane with the alkylenedimagnesium dibromide of formula

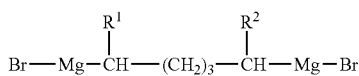

as a function of the nature of $R^1$ and $R^2$:

| $R^1$ | $R^2$ | Dialkoxysilacyclohexane formed |
|---|---|---|
| methyl | methyl | 1,1-dimethoxy-2,6-dimethylsilacyclohexane, |
| ethyl | ethyl | 1,1-dimethoxy-2,6-diethylsilacyclohexane, |
| n-propyl | n-propyl | 1,1-dimethoxy-2,6-di-n-propylsilacyclohexane, |
| isopropyl | isopropyl | 1,1-dimethoxy-2,6-diisopropylsilacyclohexane, |
| n-butyl | n-butyl | 1,1-dimethoxy-2,6-di-n-butylsilacyclohexane, |
| methyl | ethyl | 1,1-dimethoxy-2-ethyl-6-methylsilacyclohexane, |
| ethyl | n-propyl | 1,1-dimethoxy-2-ethyl-6-n-propylsilacyclohexane, |
| ethyl | isopropyl | 1,1-dimethoxy-2-ethyl-6-isopropylsilacyclohexane |
| ethyl | n-butyl | 1,1-dimethoxy-2-n-butyl-6-ethylsilacyclohexane |

By way of example, Table 2 below indicates a number of dialkoxysilacyclohexanes which may be prepared by reacting tetraethoxysilane with the alkylenedimagnesium dibromide of formula

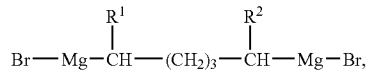

as a function of the nature of $R^1$ and $R^2$:

| $R^1$ | $R^2$ | Dialkoxysilacyclohexane formed |
|---|---|---|
| methyl | methyl | 1,1-diethoxy-2,6-dimethylsilacyclohexane, |
| ethyl | ethyl | 1,1-diethoxy-2,6-diethylsilacyclohexane, |
| n-propyl | n-propyl | 1,1-diethoxy-2,6-di-n-propylsilacyclohexane, |
| isopropyl | isopropyl | 1,1-diethoxy-2,6-diisopropylsilacyclohexane, |
| n-butyl | n-butyl | 1,1-diethoxy-2,6-di-n-butylsilacyclohexane, |
| methyl | ethyl | 1,1-diethoxy-2-ethyl-6-methylsilacyclohexane, |

-continued

| R$^1$ | R$^2$ | Dialkoxysilacyclohexane formed |
|---|---|---|
| ethyl | n-propyl | 1,1-diethoxy-2-ethyl-6-n-propylsila-cyclohexane, |
| ethyl | isopropyl | 1,1-diethoxy-2-ethyl-6-isopropylsila-cyclohexane |
| ethyl | n-butyl | 1,1-diethoxy-2-n-butyl-6-ethylsila-cyclohexane |

The reaction between the alkylenedimagnesium dibromide and the tetraalkoxysilane brings about the formation of BrMgOZ, in which Z is a radical forming part of the group of radicals R$^a$, R$^b$, R$^c$ and R$^d$.

This BrMgOZ, which is considered to be a by-product in the context of the present invention, is generally solid and in this case can be removed, for example, by filtration. Following evaporation of the solvent used, the alkoxysilacycloalkane may be purified by distillation, preferably under reduced pressure, for example between 1 and $1 \times 10^3$ mbar.

The alkylenedimagnesium dibromide may be prepared, for example, in a step B, by reacting a dibromoalkane of formula

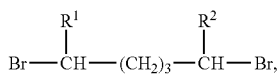

(in which R$^1$ and R$^2$ are as defined above) with magnesium, generally in the form of powder or turnings, in the presence of a solvent, for example an ether such as diethyl ether, at for example between 0 and 50° C., under pressure if appropriate—if the volatility of the species employed necessitates it, taking account of the selected temperature.

For the reaction of this step B, the reactants may be deployed with a molar ratio of the magnesium to dibromoalkane ranging preferably from 2 to 2.5, and the amount of solvent may be such that at the beginning of the reaction the dibromoalkane deployed is in a concentration ranging from 0.8 to 1.2 mol per liter of reaction medium. At the end of the reaction, it is recommended to leave the alkylenedimagnesium dibromide in solution at a concentration of more than 0.1 mol per liter, for example between 0.1 and 1.2 mol per liter, and not to attempt to isolate the alkylenedimagnesium dibromide.

The dibromoalkane of formula

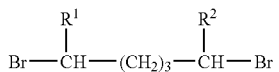

in which R$^1$ and R$^2$ are as defined above may be prepared, for example, by a first step of forming a phosphite by reacting a diol of formula

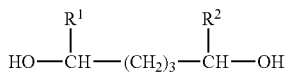

with phosphorus tribromide, PBr$_3$, preferably in the absence of a solvent, under conditions which allow the reaction to be controlled and to be maintained preferably at between 40 and 70° C., in accordance with the following scheme:

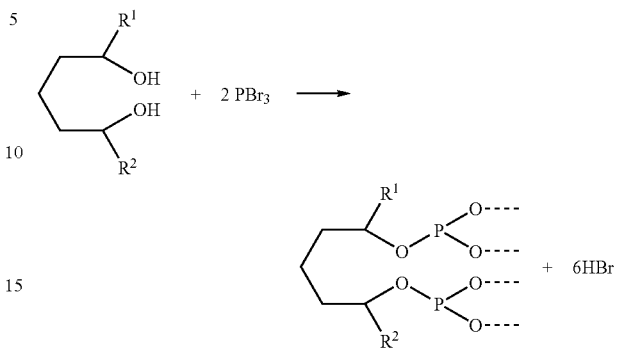

For this reaction between the diol and the PBr$_3$, the reactants may be deployed with a PBr$_3$/diol molar ratio ranging preferably from 2 to 3.

In a second step, the phosphite thus formed undergoes conversion to the dibromoalkane, the degree of conversion increasing in proportion to the HBr content of the medium. Consequently, although the medium already contains HBr originating from the reaction forming the phosphite, it is recommended, in a first phase, to add HBr to the medium, for example in an amount such that the molar ratio of the HBr added to the starting diol is from 2 to 3. By this means the medium becomes enriched in dibromoalkane and in P(OH)$_3$. Until the dibromoalkane has formed, the medium is preferably maintained at between 40 and 70° C. It is preferred to wait until the reaction of the first step is already greatly advanced (which can be perceived, for example, by the substantial weakening or even disappearance of the —OH infrared bands) before accelerating the second step by introducing additional HBr.

When the reaction is finished, the medium may be subjected to hydrolysis by adding a volume of water corresponding, for example, to from 3 to 5 times the volume of the reaction medium, followed by extraction with a hydrocarbon such as hexane, cyclohexane or pentane. Following decantation, the organic phase is separated off and neutralized with a base (for example, NaHCO$_3$ or Na$_2$CO$_3$ or KHCO$_3$) so as to obtain a pH ranging preferably from 7 to 8. Subsequently, the organic phase is preferably dried, for example using an anhydrous salt capable of becoming hydrated (for example, MgSO$_4$ or Na$_2$SO$_4$). Following filtration, the solvent may be evaporated and then the dibromoalkane may be isolated by distillation.

The diol may be prepared, for example, by reducing a diketone of the formula

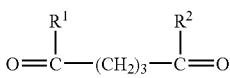

in which R$^1$ and R$^2$ are as defined above by means of an excess of a reducing agent such as, for example, [(CH$_3$OCH$_2$CH$_2$O)$_2$AlH$_2$]Na or LiAlH$_4$ or NaBH$_4$, preferably in the presence of an organic solvent, which may be an aromatic hydrocarbon such as toluene or an ether such as THF or diethyl ether.

The nature of the solvent may be selected as a function of its suitability for solubilizing the reducing agent. Preferably, the solvent is present at least in an amount sufficient to provide complete solubilization of all of the species of the medium. The maximum amount of solvent may preferably be such that the amount of diketone introduced at the start is up to $1 \times 10^{-2}$ mol per liter in the reaction medium. For this reaction, the reagents may be introduced such that the reducing agent provides an excess of reductive functions, for example an excess of from 50 to 150% of reductive functions, relative to the ketone functions to be reduced on the diketone. This reduction reaction may be conducted, for example, at from 10° C. to 50° C., although the boiling point of the solvent may constitute an upper temperature limit if the reaction is conducted at atmospheric pressure. Following this reaction, the excess reducing agent is decomposed using a base such as aqueous sodium hydroxide solution, containing for example 5% of NaOH (exercising care with regard to the exothermicity of this decomposition). The organic phase is then separated off and treated with carbon dioxide in order to precipitate the dissolved salts it contains. These salts are removed by filtration.

Finally, the diol may be isolated by evaporation from the solvent, followed, if appropriate, by one or more recrystallizations from a hydrocarbon solvent such as cyclohexane.

Where $R^1$ is identical to $R^2$, the diketone may, for example, be prepared by reacting glutaryl dichloride with an organocuprate of the formula $$R_2^1 \text{CuM}$$

in which $R^1$ is as defined above and M represents MgBr or MgCl or MgI or Li. This reaction is preferably carried out under an inert atmosphere, such as under nitrogen or argon, and at a temperature of less than or equal to −45° C., for example ranging from −78° C. to −45° C.

This reaction may be conducted preferably such that the molar ratio of the organocuprate to the glutaryl dichloride is from 1.5 to 4. Preferably, this reaction is conducted in the presence of a solvent, which may be a diethyl ether/THF mixture formed from equal volumes of these two solvents. The amount of solvent may be such that, at the beginning of the reaction, the concentration of the organocuprate is between $5 \times 10^{-2}$ and 1 mol per liter. Following reaction, the mixture may be hydrolysed, for example by means of saturated aqueous NH$_4$Cl solution, and then extracted with an organic solvent such as diethyl ether. The organic phase may then be washed with 1 N aqueous ammonia until the copper salts are removed, which is recognized by the disappearance of the blue colouration of the ammoniacal solutions of cupric complexes. Finally, following separation of the organic phase, the diketone may be isolated by evaporation of the solvent.

The organic cuprate, if it is of formula $$R_2^1 \text{CuMgBr},$$

may be prepared, for example, by reacting an alkylmagnesium compound with cuprous bromide, thus:

$$2R^1 \text{MgBr} + \text{CuBr} \rightarrow R_2^1 \text{CuMgBr},$$

For this reaction, the reagents are preferably introduced in a molar ratio of the alkylmagnesium compound to the cuprous bromide of between 1.9 and 2.1. For this reaction, a mixture of equal volumes of THF and diethyl ether is preferably present, for example in an amount such that, at the beginning of the reaction, the cuprous bromide is introduced in an amount of from $5 \times 10^{-2}$ to 1 mol per liter. The reaction may be conducted at between −78° C. and −45° C.

Where $R^1$ is an ethyl radical, the reaction is preferably carried out in the presence of lithium chloride.

Preferably, the lithium chloride is introduced in an amount which is substantially equal to the amount of alkylmagnesium compound introduced.

When $R^1$ is a radical other than the ethyl radical, it is likewise possible to use the method described in "Synthetic Procedures involving organocopper Reagents", B. H. Lipshutz, p. 283, in Organometallics in Synthesis, M. Schlosser, Ed., John WILEY and Sons, Chichester, N.Y., Brisbane, Toronto, Singapore, 1994.

In the case of asymmetric diketones, where $R^1$ is different from $R^2$, the method used is that recommended by K. ABE; H. OKAMURA, T. TSUGOSHI, N. NAKAMURA; Synthesis, 1998, 231.

In the examples below, the amount of heptane insolubles (represented by "HI") was measured by extraction of the polymer from the soluble fraction using boiling heptane for two hours in a Kumagawa-type apparatus.

EXAMPLE 17

1. Preparation of a Solution of ethylmagnesium bromide in diethyl ether

A 500-ml four-necked flask equipped with a condenser, a mechanical stirrer, a thermometer and an isobaric dropping funnel is charged under nitrogen atmosphere with 5.70 g (235 mmol; 1.1 eq.) of magnesium turnings, which are covered with 15 ml of anhydrous diethyl ether. A few drops of pure ethyl bromide are added in order to initiate the reaction, and then the remaining ethyl bromide is added dropwise (in all 23.23 g; 213 mmol; 1 eq.) in solution in 200 ml of anhydrous diethyl ether. During this addition, the reaction mixture is maintained at a temperature in the region of 5° C. When the addition is finished, it is left with stirring at ambient temperature for four hours until the magnesium turnings have almost completely disappeared.

2. Preparation of a Solution of magnesium diethylcuprate bromide in a Mixture of THF and diethyl ether A one-liter four-necked flask equipped with a mechanical stirrer, a low-temperature thermometer and an isobaric dropping funnel is charged under nitrogen atmosphere with 13.77 g; (96 mmol; 1 eq.) of CuBr and 8.14 g (192 mmol; 2 eq.) of LiCl in 240 ml of anhydrous tetrahydrofuran (THF) with vigorous stirring at 20° C. After 5 minutes of stirring at 20° C., the solution is cooled to −50° C. and then the solution of ethylmagnesium bromide prepared beforehand (192 mmol; 2 eq.) is added dropwise at −50° C. At the beginning of the addition, the solution takes on a green coloration, indicating the formation of the cuprous intermediate, then gradually darkens before becoming violet, which is the. colour of magnesium diethylcuprate bromide in this medium. The solution is maintained with stirring at −50° C. for 2 hours and is then cooled to −78° C.

3. Preparation of 3,7-nonanedione 8.11 g (48 mmol; 1 eq.) of pure glutaral dichloride are added dropwise at −78° C. to the solution of magnesium diethylcuprate bromide obtained above (96 mmol; 2 eq.). When the addition is finished, the temperature of the reaction mixture is slowly (over 1 hour) brought to −45° C.

Stirring is maintained at −45° C. for 2.5 h.

The mixture is hydrolysed with 200 ml of saturated NH$_4$Cl solution and then filtered over Celite. The aqueous phase is separated from the organic phase and is then extracted with 3 times 150 ml of ether. The organic extracts are combined and washed with 1 N aqueous ammonia until the blue coloration disappears completely. The organic phase is then washed with 50 ml of water and dried over MgSO$_4$ and the solvent is evaporated. This gives 7.2 g of 3,7-nonanedione.

4. Preparation of 3,7-nonanediol

A one-liter four-necked flask equipped with a magnetic stirrer, an isobaric dropping funnel and a thermometer is charged under nitrogen with 27 ml (90 mmol; 2 eq) of the commercial solution "Red-Al" (65% solution of [(MeOCH$_2$CH$_2$O)$_2$AlH$_2$]Na in toluene) diluted in 200 ml of anhydrous toluene. 3,7-Nonanedione (7 g; 45 mmol; 1 eq.) is dissolved in 260 ml of anhydrous toluene and then added dropwise to the Red-Al solution at room temperature for a period of approximately one hour. The solution is left with stirring at room temperature for one hour more.

After cooling using an ice bath, 15.5 ml of 5% aqueous NaOH solution are added to the solution with care, because the neutralization of the excess Red-Al is highly exothermic. The neutralization is monitored by the intensity of the evolution of hydrogen. Stirring is then stopped and the aqueous phase (loaded with aluminium hydroxide) decants to the bottom of the flask. The aqueous phase is separated from the organic phase. The organic phase is then poured into 100 ml of toluene containing a piece of dry ice. In the course of stirring, a saline precipitate is observed. The organic phase is heated at reflux until evolution of CO$_2$ stops, and is then filtered. The precipitate is washed with 2 times 5 ml of toluene. The organic extracts are combined and the solvent is evaporated on a rotary evaporator.

The 3,7-nonanediol is purified by recrystallization from cyclohexane. Its characteristics are as follows:

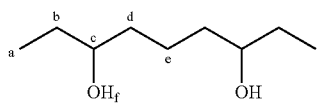

Melting point: 43° C.
Infrared (cm$^{-1}$): ν(OH): wide band between 3100 and 3700
$^1$H NMR (ppm)/CDCl$_3$ (250 MHz):
Ha: 0.90 t (6H)$^3$J$_{Ha-Hb}$=7.0 Hz
Hb+Hd+He: 1.30–1.65 m (10 H)
Hf: 2.00–2.10 m broad (2H)
Hc: 3.50 (2H)
$^{13}$C NMR (ppm)/CDCl$_3$ (62 MHz): the formation of two diastereoisomers, threo and meso, is easily indicated by the presence of two types of carbons b, c, d and e.

| 1$^{st}$ diastereoisomer: | Ca: 9.9 |
| --- | --- |
| | Ce: 21.5 |
| | Cb: 30.1 |
| | Cd: 36.5 |
| | Cc: 72.9 |
| 2$^{nd}$ diastereoisomer: | Ca: 9.9 |
| | Ce: 21.7 |
| | Cb: 30.2 |
| | Cd: 36.7 |
| | Cc: 73.1 |

5. Preparation of 3,7-dibromononane

A 100-ml four-necked flask equipped with a thermometer, a magnetic stirrer and an isobaric dropping funnel is charged under nitrogen with 5.62 g (35 mmol; 1 eq.) of 3,7-nonanediol. 7.3 ml (77 mmol; 2.2 eq.) of PBr$_3$ are then added dropwise at room temperature. The reaction is exothermic and the reaction mixture heats up to 30–35° C. then falls back to room temperature. The mixture is then heated at 60° C. for 4 hours and is left with stirring at room temperature for 15 hours.

It is subsequently heated to 60° C. for 5 hours, during which hydrobromic acid HBr is bubbled in.

The reaction mixture is poured onto 50 g of ice and then the organic phase is separated from the aqueous phase. The aqueous phase is extracted with 3 times 20 ml of hexane. The organic extracts are combined and washed with saturated NaHCO$_3$ solution until a pH of more than 7 is obtained and then with 20 ml of water. The organic phase is dried over MgSO$_4$ and the solvent is evaporated on a rotary evaporator. The 3,7-dibromononane is purified by distillation under reduced pressure (boiling at 76–82° C. under 0.3 mmHg)

6. Preparation of a Solution of nonylmagnesium 3,7-dibromide in diethyl ether A 100-ml four-necked flask equipped with a condenser, a mechanical stirrer, a thermometer and an isobaric dropping funnel is charged under nitrogen with 1.16 g (48 mmol; 2.25 eq.) of magnesium powder which is just covered with anhydrous diethyl ether. In order to activate the magnesium, a few drops of pure 1,2-dibromoethane and pure 3,7-dibromononane are added. When the reaction has started (start can easily be determined by a positive test using Michler's ketone), 6.05 g (21 mmol; 1 eq.) of 3,7-dibromononane diluted in 20 ml of anhydrous diethyl ether are added dropwise immediately without any cooling of the reaction medium. The mixture is left with stirring at room temperature for 4 h after the end of the addition.

7. Preparation of 1,1-dimethoxy-2,6-diethylsila-cyclohexane

A 250-ml four-necked flask equipped with a condenser, a magnetic stirrer, a thermometer and an isobaric dropping funnel is charged under nitrogen with 2.91 g (19.2 mmol; 0.9 eq.) of tetramethoxysilane in 20 ml of anhydrous diethyl ether. This is followed by the dropwise addition at room temperature of the ethereal solution of nonylmagnesium 3,7-dibromide, prepared beforehand, and then the solution is brought to reflux for 4 hours.

The mixture obtained is filtered under nitrogen and then centrifuged in order to remove some of the magnesium salts formed. The ether is subsequently evaporated on a rotary evaporator at 30° C. Then 10 ml of ether are added and the solution is then stirred and centrifuged, for the purpose of completely removing the residual magnesium salts. The supernatant liquid obtained is subsequently subjected to a first rapid distillation under partial vacuum (0.3 mm Hg), the distillate being trapped in a tube immersed in liquid nitrogen. It is noted that a first fraction distils at about 28° C. and that the remainder distils at between 40° C. and 120° C. without observing a fixed point. The fraction which has distilled at about 28° C. essentially comprises one or more secondary elimination products containing at least one ethylenic double bond. The other fraction is redistilled under reduced pressure (2×10$^{-2}$ mm Hg) with a microdistillation assembly, the various fractions being trapped in tubes immersed in liquid nitrogen. The following three fractions are obtained:

|            |            |
|------------|------------|
| fraction 1: | 42–48° C., |
| fraction 2: | 50–57° C., |
| fraction 3: | 58–104° C., |

Fractions 1 and 2 are mixtures containing approximately 95% of the threo and meso diastereoisomers of 2,6-diethyl-1,1-dimethoxysila-cyclohexane. Fraction 1 (480 mg) is a 91/9 threo/meso mixture (determined by gas chromatography). Fraction 2 (940 mg) is an 82/12 threo/meso mixture (determined by gas chromatography). The NMR characteristics of the majority, threo stereoisomer of 2,6-diethyl-1,1-dimethoxysilacyclohexane, as determined from fraction 1, are as follows:

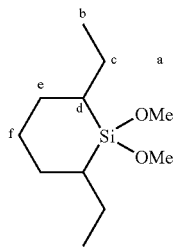

$^1$H NMR (ppm)/CDCl$_3$ (250 MHz):
Hd: 0.70–0.90 m (2H)
Hb: 0.90 t (6H) $^3J_{Hb\text{-}Hc}$=7.5 Hz
Hc: 1.20–1.35 and 1.50–1.65 two multiplets (4H)
Hf: 1.35–1.45 m (2H)
He: 1.50–1.60 and 1.70–1.75 two multiplets (4H)
Ha: 3.55 s (6H)
$^{13}$C NMR (ppm)/CDCl$_3$ (62 MHz)
Cb: 13.3
Cc: 21.6
Cf: 23.2
Cd: 24.7
Ce: 30.1
Ca: 50.6

EXAMPLE 18

A 3.6-liter stainless steel reactor equipped with a stirrer system and a temperature regulator is first purged with nitrogen and then charged with 5.7 l (S.T.P.) of hydrogen, then 2.4 liters of liquid propylene, then 30 millimol of triethylaluminium in the form of a 1.5 mol/liter solution in hexane, then 1.5 millimol of 1,1-dimethoxy-2,6-diethylsila-cyclo-hexane in the form of a 0.2 mol per liter solution in hexane (giving an Al/Si molar ratio of 20). Subsequently, with stirring, 40 mg of a solid catalytic component prepared as in Example 12 of the Patent U.S. Pat. No. 5,212,132 are introduced, after which the temperature of the reactor is raised to 70° C. over 10 minutes and held at this temperature for one hour. The reactor is subsequently cooled and decompressed. A polypropylene having a heptane insolubility index of 98.8 was obtained with a productivity of 52,000 g of polymer per g of solid catalytic component.

EXAMPLE 19

Comparative

The procedure of Example 2 is repeated except that the 1,1-dimethoxy-2,6-diethylsilacyclohexane is replaced by the same number of moles of 1,1-dimethoxy-2-ethylsilacyclohexane.

A polypropylene having a heptane insolubility index of 97.9 was obtained with a productivity of 40,000 g of polymer per g of solid catalytic component.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated.

What is claimed is:
1. Process for preparing a dialkoxysilacyclohexane of formula

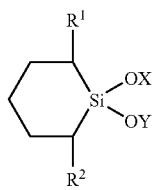

in which R$^1$ and R$^2$, which may be identical or different, represent alkyl radicals containing 1 to 5 carbon atoms, and X and Y, which may be identical or different, are alkyl radicals containing 1 to 6 carbon atoms, the method comprising reacting an alkylenedimagnesium dibromide of formula

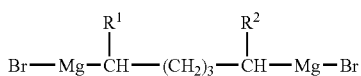

with a tetraalkoxysilane of formula (OR$^a$)(OR$^b$)(OR$^c$)(OR$^d$)Si, in which R$^a$, R$^b$, R$^c$, and R$^d$ are selected from the same group as X and Y, at least one of the radicals R$^a$, R$^b$, R$^c$, and R$^d$ being identical to X, and at least one of the radicals R$^a$, R$^b$, R$^c$, and R$^d$ being identical to Y.

2. Process according to claim 1, wherein the alkylenedimagnesium dibromide is prepared by a process comprising reacting a dibromoalkane of formula:

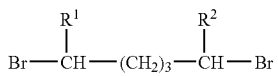

with magnesium.

* * * * *